(12) United States Patent
Ries et al.

(10) Patent No.: US 8,623,021 B2
(45) Date of Patent: Jan. 7, 2014

(54) FACET JOINT REAMER

(75) Inventors: Wolfgang Ries, Linkenheim (DE);
Mathias Notheis, Forst (DE)

(73) Assignee: Joimax GmbH, Karlsruhe (DE)

( * ) Notice: Subject to any disclaimer, the term of this patent is extended or adjusted under 35 U.S.C. 154(b) by 1121 days.

(21) Appl. No.: 11/585,869

(22) Filed: Oct. 25, 2006

(65) Prior Publication Data

US 2007/0123892 A1  May 31, 2007

(30) Foreign Application Priority Data

Oct. 26, 2005  (DE) ...................... 20 2005 016 762 U

(51) Int. Cl.
*A61B 17/00*  (2006.01)

(52) U.S. Cl.
USPC ..................... 606/79; 606/82; 606/83; 606/84

(58) Field of Classification Search
USPC ................. 606/79–86 R, 167, 178, 184, 185; 407/29.1, 29.13, 29.15; 408/204, 206
See application file for complete search history.

(56) References Cited

U.S. PATENT DOCUMENTS

| | | | | |
|---|---|---|---|---|
| 2,062,257 A | * | 11/1936 | Douglas et al. ............... | 408/204 |
| 2,429,356 A | | 10/1947 | Hicks | |
| 4,069,824 A | * | 1/1978 | Weinstock ...................... | 606/82 |
| 4,559,936 A | * | 12/1985 | Hill ................................. | 606/79 |
| 4,696,308 A | * | 9/1987 | Meller et al. .................. | 600/567 |
| 4,782,833 A | * | 11/1988 | Einhorn et al. ................ | 606/80 |
| 4,803,982 A | * | 2/1989 | Baker ............................ | 606/173 |
| 5,190,548 A | | 3/1993 | Davis | |
| 5,312,408 A | * | 5/1994 | Brown ............................ | 606/80 |
| 5,330,480 A | * | 7/1994 | Meloul et al. .................. | 606/80 |
| 5,346,497 A | * | 9/1994 | Simon et al. .................. | 606/107 |
| 5,697,935 A | * | 12/1997 | Moran et al. .................. | 606/104 |
| 5,961,522 A | | 10/1999 | Mehdizadeh | |
| 6,200,322 B1 | * | 3/2001 | Branch et al. .................. | 606/96 |
| 6,235,035 B1 | | 5/2001 | Boukhris | |
| 6,322,564 B1 | | 11/2001 | Surma | |
| 6,451,023 B1 | * | 9/2002 | Salazar et al. ............. | 606/86 R |
| 6,682,535 B2 | * | 1/2004 | Hoogland ....................... | 606/80 |
| 6,942,669 B2 | * | 9/2005 | Kurc ............................... | 606/80 |
| RE40,796 E | * | 6/2009 | O'Neill ......................... | 600/567 |
| 2002/0091387 A1 | * | 7/2002 | Hoogland ....................... | 606/61 |
| 2004/0267268 A1 | * | 12/2004 | Gillespie et al. ............... | 606/80 |
| 2007/0073301 A1 | * | 3/2007 | Lieberman ..................... | 606/79 |
| 2007/0267268 A1 | * | 11/2007 | Baehr et al. ................. | 192/84.6 |
| 2008/0167652 A1 | * | 7/2008 | Reinhard ....................... | 606/80 |

FOREIGN PATENT DOCUMENTS

| | | |
|---|---|---|
| DE | GM 80 13 521 U1 | 8/1980 |
| DE | 88 06 721 U1 | 8/1988 |
| DE | G 88 06 721.1 U1 | 8/1988 |
| DE | 296 16 633 U1 | 11/1996 |
| DE | 692 17 689 T2 | 7/1997 |
| DE | 698 22 829 T2 | 1/2005 |
| DE | 699 17 683 T2 | 7/2005 |
| DE | 20 2005 016763 U1 | 11/2006 |
| EP | 0 951 872 A2 | 10/1999 |
| JP | 2003 245283 A | 9/2003 |
| WO | WO 2004/032767 A | 4/2004 |
| WO | WO 2004/060170 * 7/2004 ............. A61B 17/00 |  |

* cited by examiner

*Primary Examiner* — Kevin Truong
*Assistant Examiner* — Matthew Lawson
(74) *Attorney, Agent, or Firm* — McGlew and Tuttle, P.C.

(57) ABSTRACT

In a facet joint reamer with a shank and teeth at the distal end, the distal end is widened compared with the remainder of the shank.

18 Claims, 5 Drawing Sheets

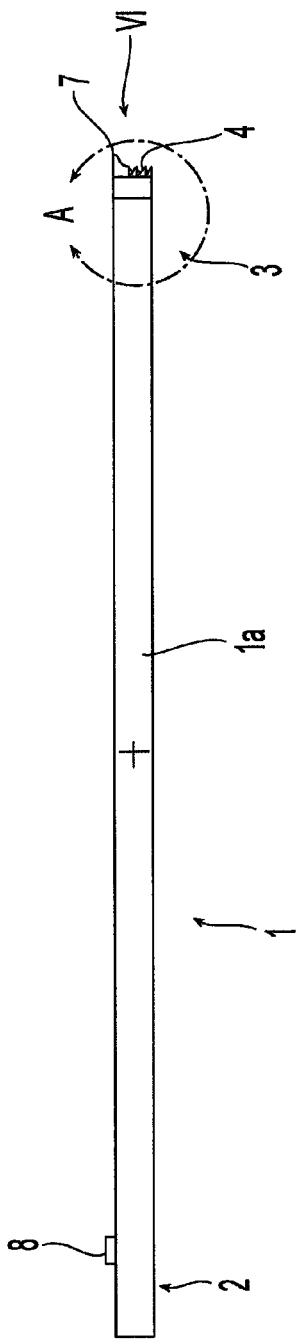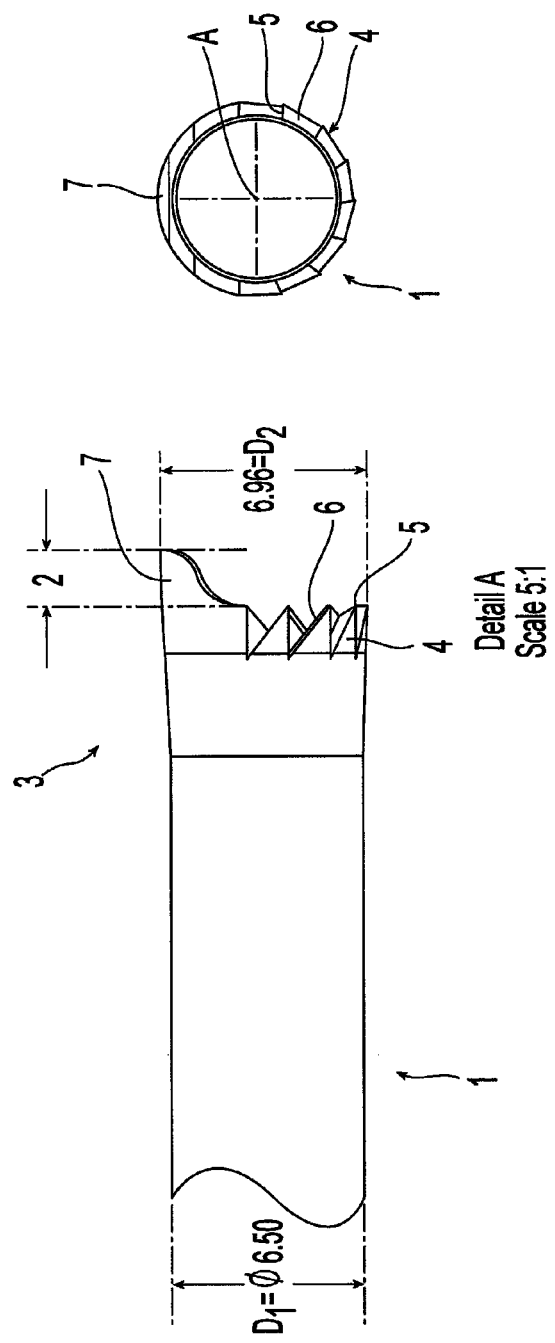

FACET JOINT REAMER

FIELD OF THE INVENTION

The invention relates to a facet joint reamer having a shank and teeth at the distal end.

BACKGROUND OF THE INVENTION

Such a facet joint reamer, also commonly known as a facet joint milling cutter, is known from DE 699 17 683 T2. The known reamer has a hollow cylindrical shank, a handle at its rear, proximal end and teeth at its front end.

Such a reamer is used for cutting out vertebral components in the vicinity of a lateral process of a vertebral column vertebra in order to create postero-lateral access to strangulated nerve roots of the central nervous system. Through said access it is then possible to remove intervertebral disk pulp tissue and other tissue types (capsular, cicatricial and ring tissue), because they press on the nerve roots. Said process of a vertebra forms the facet joint with an adjacent process of an adjacent vertebra.

The microinvasive surgery method for the decompression of strangulated nerve roots using such a facet joint reamer is highly successful. However, it has been found that the bone material cut out by the reamer is not adequately removed from the cutting out area.

An object of the invention is therefore to so further develop such a facet joint reamer that it is possible to reliably remove cut out bone material.

SUMMARY OF THE INVENTION

According to the invention this object is solved in the case of a facet joint reamer of the aforementioned type in that the distal end of the reamer is widened compared with the shank diameter.

As a result of the widening of the distal end of the facet joint reamer, particularly over the height of the reamer teeth, but preferably up to roughly twice the height of the reamer teeth, the entry of cut out bone material into the reamer interior is improved and can, if necessary, be sucked off. The widening extends constantly and continuously from the reamer shank cross-section to the maximum widening at the front end of the teeth and is between 0.2 and 0.6 mm, preferably 0.4 mm, so that the reamer diameter at the front end of the teeth is between 0.2 and 0.6 mm, preferably 0.4 mm more than the cylindrical shank diameter.

An extremely preferred facet joint reamer is characterized by a lip axially projecting over the teeth and extending over a partial circumference, the extension arc or angle being between 140 and 160°, preferably 150°. The axial height of the lip is preferably in a range 1 to 3 mm.

The lip is deburred and its edges rounded. It is used for protecting the nerve when the reamer is used close to the latter, so that said nerve is not injured by the cutting process. For orientation purposes the proximal, i.e. the teeth-remote end of the reamer is provided with a marking, e.g. an elevated rib corresponding to the lip position.

Particularly in the case of a reamer constructed with such a lip said reamer is not completely rotated and is instead rotated backwards and forwards in oscillating manner, so that the teeth are always in engagement with the bone material.

BRIEF DESCRIPTION OF THE DRAWINGS

Further advantages and features of the invention can be gathered from the claims and subsequent description of an embodiment of the invention with reference to the attached drawings, wherein show:

FIG. 4 A side view of a particularly preferred development of an inventive reamer.

FIG. 5 The distal end of the reamer of FIG. 4 on a larger scale.

FIG. 6 A front view corresponding to VI in FIG. 4 of said reamer.

DETAILED DESCRIPTION OF THE DRAWINGS

Figure 1:
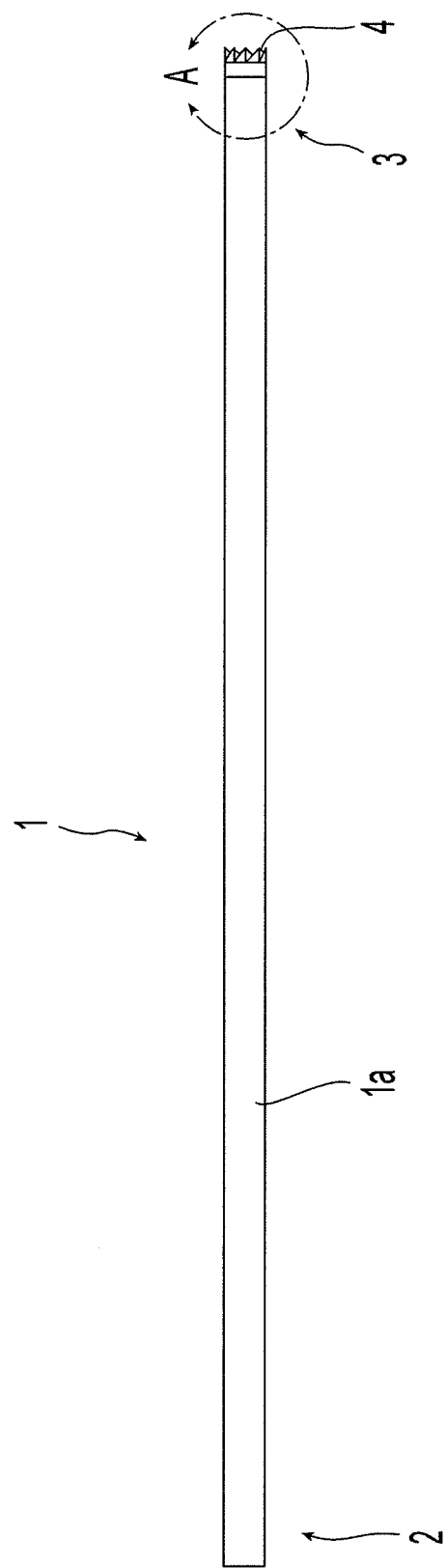
FIG. 1 An inventive reamer in side view.

The facet joint reamer according to the invention has a shank 1a, preferably with a length between 18 and 25 cm and in the embodiment shown roughly 21 cm. At its rear or surgeon-pointing, proximal end 2 the reamer 1 is either provided with a handle or with a fastening device for the releasable fastening to a handle, the latter preferably being made from plastic. Neither the fastening device nor the handle are shown in detail.

Teeth 4 are located at its front or distal end 3. In the embodiment shown the teeth 4 have an asymmetrical construction. On viewing the front end according to FIG. 3, the front flank 5, parallel to axis A, is directed counterclock-wise G, whereas the rear flank 6 is chamfered and has an inclination angle of 35 to 45°, preferably approximately 40° to axis A. In the rotation direction when working the front flank 5 is the active, cutting flank.

Figure 2:
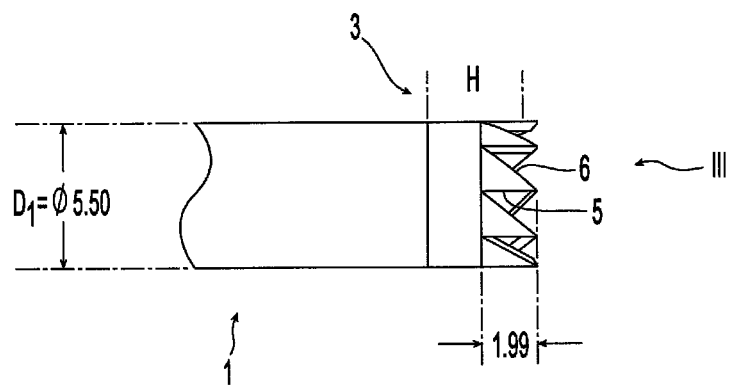
FIG. 2 A larger scale representation of the distal or head end of the reamer of FIG. 1.
Figure 3:
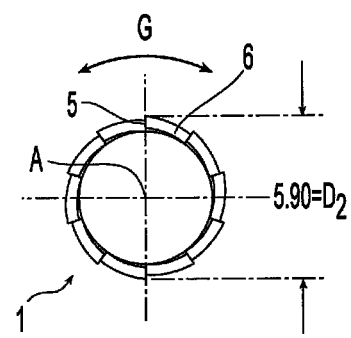
FIG. 3 A view of the distal end of the reamer of FIG. 2 along arrow III thereof.

As can in particular be gathered from FIGS. 2 and 3, the front end of reamer 1 is widened compared with the diameter of shank 1a. Whereas in the embodiment shown the shank has a diameter of 5.5 mm, the distal end of the reamer has a diameter of 5.9 mm in the vicinity of teeth 4. Thus, there is a 0.4 mm widening. Preferably the widening is in the range approximately 0.8 mm or 2% of the diameter up to 0.6 mm with a tolerance of 0.01 mm. Diameter $D_1$ of shank 1a up to diameter $D_2$ of the front end of teeth 4 extends over a height H, i.e. 2 mm, so that the height H of the widening area is approximately 4 mm and can preferably be up to 6 mm.

As a result of the widening the cut out bone material enters the reamer interior and therefore out of the working area and can consequently be removed from the patient's body, e.g. by sucking through the reamer interior.

FIGS. 4 to 6 show a further extremely preferred development of the inventive reamer. To the extent that identical parts are present, the same reference numerals are used. In connection with said common parts reference is made to the explanations concerning FIGS. 1 to 3.

Unlike in the reamer of FIGS. 1 to 3, reamer 1 of FIGS. 4 to 6 has a lip 7 projecting axially over a partial circumference or arc of the shank jacket. The arcuate extension runs over an angle of 150° in the embodiment shown and the height of lip 7 over and beyond the crests of the teeth and independently of the reamer diameter is approximately 2 mm. The lip is deburred and the edges rounded. Thus, an adjacent nerve is protected when working in the vicinity of a nerve by lip 7, so that the cutting operation does not injure the nerve.

Figure 7:
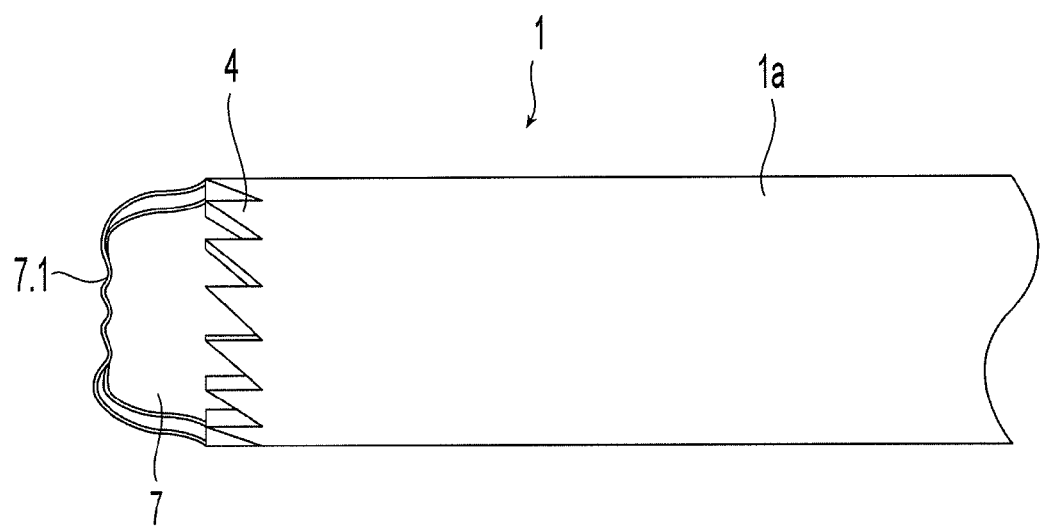
FIG. 7 A front end of an inventive reamer with a rasp-formed lip.

In the development of FIG. 7 the front end of the lip 4 is in the form of a rasp 7.1 with wavy teeth. Thus, in the case of swivelling movements under pressure soft tissue parts, such as periosteum can be removed, whereas harder nerve skin is not damaged by such a rasp 7.1.

For orientation purposes the proximal end 2 of reamer 1 is provided with a marking 8 corresponding to the position of lip 7, i.e. is axially aligned therewith.

The reamer according to the invention is used in the manner described hereinafter relative to FIGS. 8 and 9.

Figure 8:
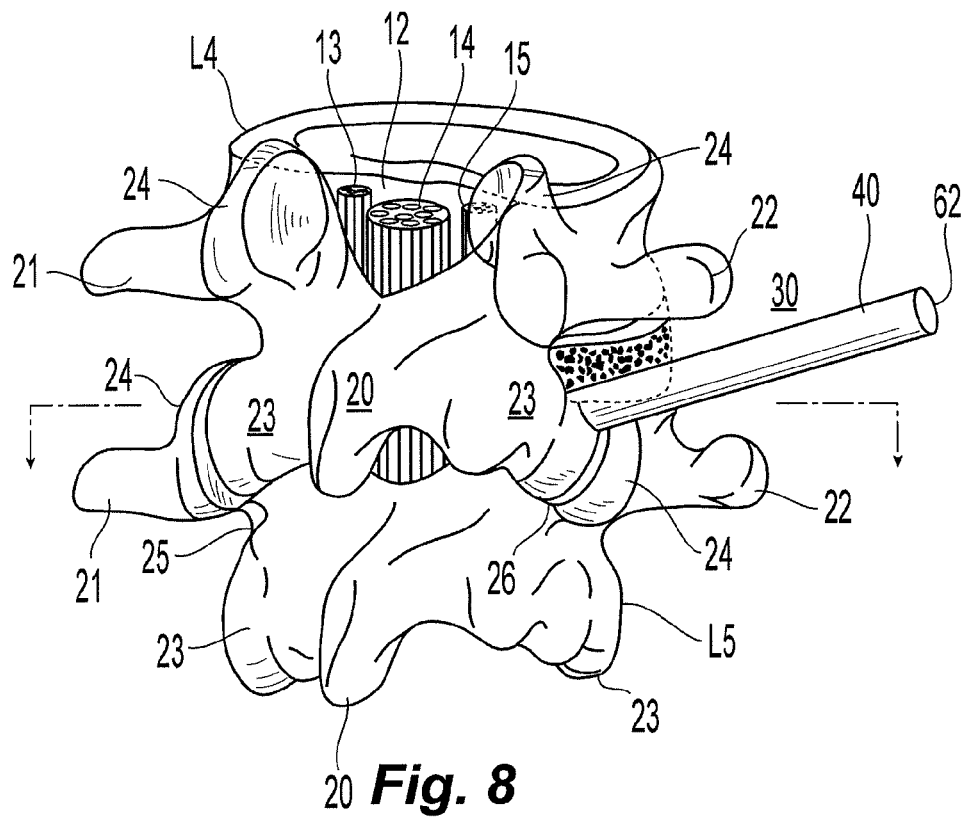
FIG. 8 A rear view of two adjacent lumbar vertebrae of the human vertebral column.
Figure 9:
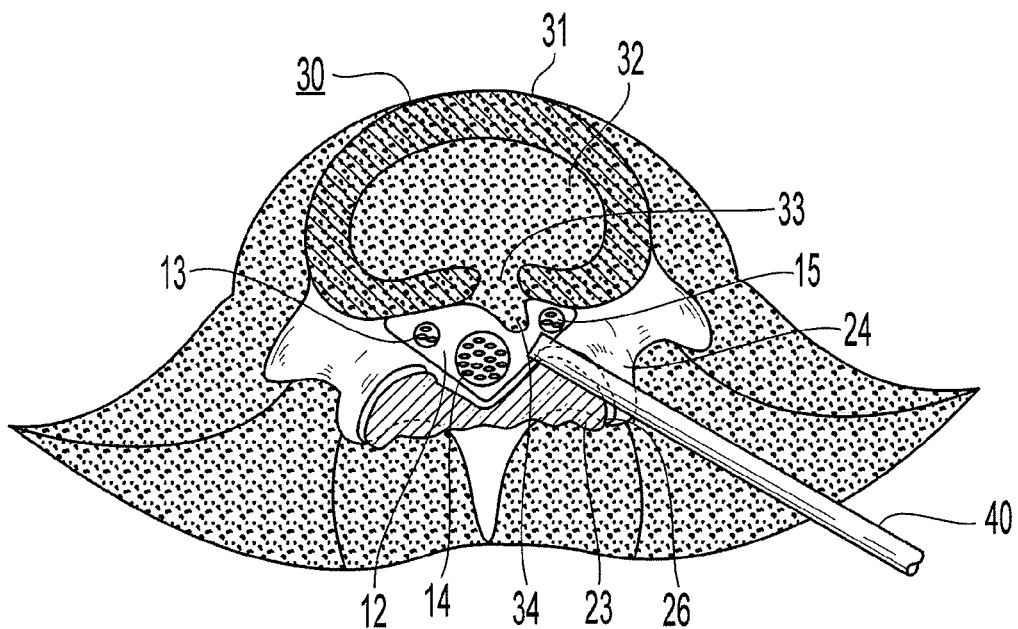
FIG. 9 A part sectional view of the spinal intervertebral disks between the two vertebrae in FIG. 7.

FIG. 8 shows in exemplified manner the fourth and fifth lumbar vertebrae L4, L5 and between the same an intervertebral disk 30 with a strangulation 33 at the fibrous ring 31 immediately to the right of the central axis of the vertebral column with an extrusion 34 of intervertebral disk pulp tissue into the vertebral canal FIG. 9.

Nerve structures 13, 14, 15 are diagrammatically illustrated in the interior of the vertebral canal 12. Each vertebra L4, L5 has a spinous process 20 and a left and right-hand transverse process 22, left and right-hand, lower, joint-forming processes 23 and left and right-hand, upper, joint-forming processes 24, the left and right-hand joint between the upper and lower lumbar vertebra L4, L5, referred to as the facet joint 26 being formed by in each case the lower processes 23 of the upper vertebra L4 and the upper processes 24 of the lower vertebra L5.

The reamer according to the invention is used in the following way:

Firstly a hollow needle or probe with an external diameter of approximately 1.25 mm is advanced into a position adjacent to the strangulation. A guide wire is then passed through the lumen until its distal end projects somewhat over the end of the hollow probe. The hollow probe is then removed, whereas the guide wire remains in place. A guide rod with an external diameter of 2.5 mm (also constructed as a dilator) is advanced over the guide wire until the conical end of the guide rod (external diameter 2.5 mm) is at the facet joint 26. A guide sleeve (external diameter 3.8 mm), which is conical at the distal end, is then engaged over the guide rod for further tissue dilation and reamer guidance. Whilst holding the guide rod with guide sleeve in this position an inventive reamer with a small diameter approximately the same as the internal diameter 4.2 mm, external diameter 5.0 mm is advanced over the guide rod and guide sleeve 52 until the distal reamer end engages on the surface of the facet joint 26.

The surgeon then rotates, e.g. manually and preferably in oscillating manner the handle located at the reamer end close to him, so that in the protuberance 23 of vertebra L4 a channel is produced. This step is repeated with guide rods, guide sleeves and reamers with a larger diameter until an adequate channel diameter is obtained in order to receive a working cannula with a lumen which is sufficiently large to be able to guide through not only forceps, but also an endoscope. The strangulation 33 is then removed with the forceps, optionally under endoscopic observation.

Reference Numerals List
- 1 Reamer
- 1a Shank
- 2 Proximal end
- 3 Distal end
- 4 Teeth
- 5 Front flank
- 6 Rear flank
- 7 Lip
- 7.1 Rasp
- 12 Vertebral canal
- 13, 14, 15 Nerve structures
- 20 Spinous process
- 22 Transverse process
- 23, 24 Processes
- 26 Facet joint
- 30 intervertebral disk
- 31 Fibrous ring
- 33 Strangulation
- 34 Extrusion
- A Axis
- $D_1$, $D_2$ Diameter
- G Counterclockwise (=rotation direction)
- H Height
- L4, L5 Lumbar vertebrae

The invention claimed is:

1. A facet joint reamer for creating a postero-lateral access through a vertebral column, the facet joint reamer comprising:
    a shank extending along a rotary axis and having a distal end portion extending from a main shank portion, said shank being rotatable about said rotary axis;
    a plurality of teeth, each tooth of said plurality of teeth being adjacent to another tooth of said plurality of teeth, at least a portion of said distal end portion forming said plurality of teeth at said distal end portion of said shank, said plurality of teeth extending around at least a teeth section of a circular circumference of said shank centered on the rotary axis, each of the teeth having a front flank extending parallel to the rotary axis, wherein the distal end portion is wider in diameter than the main shank portion; and
    a lip, at least another portion of said distal end portion forming said lip at a distal end of said shank, said lip extending over a part of the circumference and said lip projecting along said rotary axis distally over the teeth, said lip being integrally connected to said distal end of said shank, said lip encompassing between 140 and 160 degrees of said circular circumference of said shank, said teeth section comprising a remainder of said circular circumference of said shank.

2. The reamer according to claim 1, wherein the wider-diameter distal end portion defines a circumferential widening that extends at least over a height of the teeth.

3. The reamer according to claim 2, wherein the widening extends over double the height of the teeth.

4. The reamer according to claim 2, wherein the widening is continuous and constant from the diameter of the main shank portion to a maximum diameter of the widening at crests of the teeth.

5. The reamer according to claim 4, wherein the widening extends over a length between 4 and 6 mm to the crests of the teeth.

6. The reamer according to claim 5, wherein the widening at the crests is 0.4 mm.

7. The reamer according to claim 1, wherein the lip projects over the teeth by 1 to 3 mm.

8. The reamer according to claim 1, wherein at least a front end of the lip comprises a rasp.

9. The reamer according to claim 1, wherein the lip extends 150 degrees.

10. The reamer according to claim 1, wherein said shank is integrally connected with said distal end to form a one-piece shank structure.

11. A facet joint reamer for creating a postero-lateral access through a vertebral column, the facet joint reamer comprising:
    a shank extending along a rotary axis, said shank being rotatable about said rotary axis, said shank having a distal end portion and a main shank portion, said distal end portion extending from said main shank portion, said distal end portion having a distal end surface, said distal end surface defining a lip and defining a plurality of teeth, wherein said lip is integrally connected to said distal end portion of said shank, each of said plurality of teeth being adjacent to another one of said plurality of teeth, said plurality of teeth defining a first circumferential end portion of said shank, said lip defining a second circumferential end portion of said shank, said first circumferential portion being centered with respect to the rotary axis, said second circumferential end portion extending over an arc of 140 to 160 degrees of a circumference of said distal end surface, said first circumferential end portion extending over a remainder of said circumference of said distal end surface, each of said teeth having a front flank extending parallel to the rotary axis, wherein the distal end portion has a distal end portion diameter, said main shank portion having a main shank portion diameter, said distal end portion diameter being greater than said main shank portion diameter, each of said teeth having a tooth end, said lip having a lip end, said lip end projecting distally beyond said tooth end of each of said teeth along the rotary axis, at least a portion of said lip extending between one of said plurality of teeth and another one of said plurality of teeth, said lip defining a means for engaging a nerve structure such that said lip maintains the nerve structure at a spaced location from said plurality of teeth.

12. The reamer according to claim 11, wherein the wider-diameter distal end portion defines a circumferential widening that extends at least over a height of the teeth.

13. The reamer according to claim 12, wherein the widening extends over double the height of the teeth.

14. The reamer according to claim 12, wherein the widening is continuous and constant from the diameter of the main shank portion to a maximum diameter of the widening at crests of the teeth.

15. The reamer according to claim 14, wherein the widening extends over a length between 4 and 6 mm wider to the crests of the teeth.

16. The reamer according to claim 15, wherein the widening at the crests is 0.4 mm.

17. The reamer according to claim 11, wherein the lip projects over the teeth by 1 to 3 mm.

18. The reamer according to claim 11, wherein at least a front end of the lip is configured as a rasp, wherein the lip extends over an arc of 150 degrees.

* * * * *